United States Patent
Türk et al.

(10) Patent No.: US 10,240,110 B2
(45) Date of Patent: *Mar. 26, 2019

(54) POLYURETHANE THICKENER

(75) Inventors: Holger Türk, Mannheim (DE); Volker Wendel, Seeheim-Jugenheim (DE)

(73) Assignee: BASF SE, Ludwigshafen (DE)

( * ) Notice: Subject to any disclaimer, the term of this patent is extended or adjusted under 35 U.S.C. 154(b) by 417 days.

This patent is subject to a terminal disclaimer.

(21) Appl. No.: 12/991,302

(22) PCT Filed: May 6, 2009

(86) PCT No.: PCT/EP2009/055439

§ 371 (c)(1),
(2), (4) Date: Nov. 5, 2010

(87) PCT Pub. No.: WO2009/135856

PCT Pub. Date: Nov. 12, 2009

(65) Prior Publication Data

US 2011/0166291 A1    Jul. 7, 2011

(30) Foreign Application Priority Data

May 6, 2008  (EP) .................... 08155673

(51) Int. Cl.
| | | |
|---|---|---|
| C11D 3/37 | (2006.01) | |
| C08G 18/28 | (2006.01) | |
| C09D 7/43 | (2018.01) | |
| C08G 18/10 | (2006.01) | |
| C08G 18/24 | (2006.01) | |
| C08G 18/73 | (2006.01) | |
| C08G 18/48 | (2006.01) | |
| A61Q 19/00 | (2006.01) | |
| A61K 8/87 | (2006.01) | |
| C08L 75/08 | (2006.01) | |

(52) U.S. Cl.
CPC .............. *C11D 3/3726* (2013.01); *A61K 8/87* (2013.01); *A61Q 19/00* (2013.01); *C08G 18/10* (2013.01); *C08G 18/24* (2013.01); *C08G 18/283* (2013.01); *C08G 18/4833* (2013.01); *C08G 18/73* (2013.01); *C09D 7/43* (2018.01); *C08L 75/08* (2013.01)

(58) Field of Classification Search
CPC .... C11D 3/3726; C08G 18/283; C08G 18/10; C08G 18/24; C08G 18/73; C08G 18/4833; C09D 7/43; A61Q 19/00; A61K 8/87; C08L 75/08
USPC ......... 524/591; 528/49, 55, 56, 76; 529/904; 560/158

See application file for complete search history.

(56) References Cited

U.S. PATENT DOCUMENTS

| | | | |
|---|---|---|---|
| 4,079,028 A | | 3/1978 | Emmons et al. |
| 4,155,892 A | | 5/1979 | Emmons et al. |
| 4,332,927 A | * | 6/1982 | Simone ........................... 528/58 |
| 4,704,446 A | * | 11/1987 | Goel ................................ 528/78 |
| 5,026,814 A | * | 6/1991 | Re et al. ......................... 528/61 |
| 2004/0028742 A1 | * | 2/2004 | Bigorra Llosas et al. ..... 424/486 |

FOREIGN PATENT DOCUMENTS

| | | |
|---|---|---|
| CN | 1443208 A | 9/2003 |
| EP | 0495373 A2 | 7/1992 |
| EP | 0639595 A1 | 2/1995 |
| EP | 0725097 A1 | 8/1996 |
| EP | 1013264 A1 | 6/2000 |
| EP | 1584331 | 10/2005 |
| JP | 2002-265779 A | 9/2002 |
| WO | WO-2002/006369 A1 | 1/2002 |
| WO | WO-2006/002813 A2 | 1/2006 |

OTHER PUBLICATIONS

"Investigating the Effect of Hydrophobic Structural Parameters on the Thickening Properties of HEUR Associative Copolymers," Mohammad Barmar et al.; European Polymer Journal; Pergamon Press Ltd, 2005, 619-626.

English-language translation of International Preliminary Report on Patentability issued in related International Application No. PCT/EP2009/055439, dated Nov. 25, 2010.

* cited by examiner

*Primary Examiner* — Rabon A Sergent
(74) *Attorney, Agent, or Firm* — Drinker Biddle & Reath LLP

(57) ABSTRACT

The present invention relates to novel polyurethanes and to mixtures of such polyurethanes, to processes for their preparation, to their use for producing preparations comprising water and to preparations which comprise the polyurethanes. In particular, the invention relates to water-dispersible polyurethane with an essentially linear backbone composed of alternating hydrophilic and hydrophobic sections.

3 Claims, No Drawings

POLYURETHANE THICKENER

CROSS REFERENCE TO RELATED APPLICATIONS

This application is a national stage application under 35 U.S.C. § 371 of PCT/EP2009/055439, filed May 6, 2009, which claims benefit to European application 08155673.0, filed May 6, 2008, the entire disclosures of which are hereby incorporated by reference.

The present invention relates to polyurethanes (PU) and to mixtures of such polyurethanes PU according to the invention, to processes for the preparation of PU, to the use of PU for producing preparations comprising water and to preparations which comprise polyurethanes PU. In particular, the invention relates to water-dispersible polyurethane (PU) with an essentially linear backbone composed of alternating hydrophilic and hydrophobic sections, where a. the two terminal sections (T) are hydrophobic,
b. each section T is directly attached to a hydrophilic section (S),
c. each section S is directly attached to at least one hydrophobic section (D) on at least one side, and
d. where at least one hydrophilic section (P) is present, where at least one hydrophobic section D separates two sections P if more than one section P is present, and the polyurethane comprises at least three hydrophilic sections, and the ratio of the molecular weights of each hydrophilic section S to the molecular weight of each hydrophilic section P is from 1:1.4 to 1:140, the at least two hydrophobic sections D are aliphatic diisocyanate radicals and the at least one hydrophilic section P is a polyether radical with a molecular weight of at least 1500 g/mol, or a mixture of different polyurethanes PU.

The present invention further comprises combinations of the embodiments specified below.

Polyurethanes are polymers which can be prepared, for example, by reacting alcohols (e.g. diols) with diisocyanates.

These compounds have been used for decades in the printing industry. Polyurethanes with very different physicochemical properties are obtained corresponding to the choice of starting materials and the stoichiometric ratio of the starting materials. Polyurethanes PU according to the invention are polymers which are formed by reacting alcohol alkoxylates and/or polyether polyols with isocyanates or polyisocyanates, and are also referred to below as polyether urethanes.

Thickeners are used widely for increasing the viscosity of aqueous preparations, for example in the fields of cosmetics, human and animal nutrition, pharmacy and for detergents, paints and coatings. Inter alia, polyurethanes are also known as thickeners.

For example, polyurethane solutions or dispersions in water-dilutable aqueous or predominantly aqueous phase are referred to by the person skilled in the art as HEUR thickeners (the acronym HEUR is derived from "hydrophobically modified ethylene oxide urethane copolymer"), and have been used for a relatively long time in highly diverse fields of application for thickening water-based emulsion paints. The action principle of the thickening effect of the HEUR thickeners is assumed to be that the polyethylene glycol segments ensure the water compatibility and the hydrophobic segments construct a viscosity-imparting three-dimensional molecular association via an association with one another and also with dispersed binder particles of the emulsion paint to be thickened therein.

However, the use of the known thickeners is associated with disadvantages, depending on the preparation to be thickened. Thus, the thickening effect and the salt stability of the thickeners may not be satisfactory and their incorporation into the preparation to be thickened may be hindered. For example, it is known that many thickeners, such as, for example, crosslinked (hydrophobically modified) polyacrylic acids in the neutralized state and also polyurethane-containing thickeners react very sensitively to salt or surfactant or a mixture thereof. The addition of salt can lead to an abrupt and drastic decrease in viscosity. It is therefore unusual, for example, to use these polymers in shampoo formulations as viscosity-imparting agents. No significant viscosity increase can be brought about on account of the salt concentrations present therein (surfactants, surfactant mixtures, NaCl as impurity in surfactants). The presence of cationic auxiliaries can lead to complex formation and precipitate. Thickeners are also used in the field of cosmetic preparations. However, no salt-stable thickeners are currently known for cosmetic preparations which, coupled with a good thickening power in the presence of salt, also lead to preparations with good texture and pleasant feel on the skin. Compatibility with numerous other auxiliaries, in particular with salts and surfactants and also the incorporability of the thickener itself, and also of the further auxiliaries should be provided. Furthermore, the thickened preparations must have constant rheology and physical and chemical quality even upon long-term storage, and in the case of temperature and pH changes. Finally, these thickeners should still be able to be produced cost-effectively and without a notable impact on the environment.

The specifications U.S. Pat. Nos. 4,079,028 and 4,155,892 disclose, inter alia, linear polyurethane thickeners. The preparation of these polyurethane thickeners takes place in the presence of polymerization catalysts.

EP 1 584 331-A and EP 1 013 264 B disclose polyurethane thickeners for cosmetic preparations. These are prepared in a single-stage process through reaction without a diluent from polyol, polyisocyanate and fatty alcohol, which, if desired, may be ethoxylated. According to the cited specifications, the viscosity of a preparation which comprises these thickeners does not change if the salt concentration in the preparation changes.

WO 2006/1 002 813 A WO 2006/002 813 A discloses polyurethane thickeners for various applications in aqueous media. These thickeners are prepared from hydrophilic polyols with at least two hydroxy groups, one or more hydrophobic compounds, e.g. long-chain alcohols and at least difunctional isocyanates. Here, an excess of NCO groups is used. The catalyst used in the preparation may be tin-containing, zinc-containing or an amine. EP 0 725 097 B discloses polyurethane thickeners for whose preparation polyethers, produced through the alkoxylation of alcohols or alkylphenols, are reacted with polyisocyanates, where the ratio of NCO to OH equivalents is in the range from 0.9:1 to 1.2:1. These thickeners are proposed for use in the sector of low shear forces, e.g. for the flow of aqueous emulsion paints.

It was an object of the present invention to provide novel polyurethanes which should be dispersible in water. It was a further object of the present invention to provide novel thickeners for preparations comprising water. It was yet a further object of the present invention to provide novel thickeners for preparations comprising water, for example for cosmetic preparations, which lead to the highest possible viscosities. Moreover, the object was to find thickeners which produce stable or even increased viscosities in preparations comprising water in the presence of salt. It was furthermore the object to provide polyurethane thickeners with the described properties which are additionally tin-free since this is desired for cosmetic applications. It was a further object to provide a process for the preparation of water-dispersible polyurethanes in which molecules with the greatest possible structural uniformity are formed and undesired by-products or undesired crosslinking reactions are reduced although the process operates without the tin-containing catalysts customary in polyurethane chemistry. It was furthermore the object to provide a preparation process for water-dispersible polyurethanes in which exclusively aliphatic isocyanate components are used. Furthermore, it was an object to provide a preparation process for water-dispersible polyurethanes in which the lowest possible amounts of isocyanates are used.

The water-dispersible polyurethanes PU of the present invention, the processes for their preparation according to the invention, the use according to the invention of said polyurethanes in preparations comprising water and preparations comprising water which comprise the polyurethanes according to the invention represent solutions for the objects described above.

According to the invention, the polyurethanes are dispersible in water. According to the invention, this comprises that they are also able to emulsify in water or to completely or partially dissolve in water.

Preferably, the polyurethanes PU according to the invention have the property that, in a dispersion in water at concentrations between 0.1 g/l and 10 g/l, they form micelles with an average particle size of less than or equal to 200 nm, in particular less than or equal to 100 nm (can be determined by means of dynamic light scattering as described below). The term nanodispersible polyurethanes can therefore also be used. The critical micelle concentration is accordingly preferably less than 0.1 g/l.

The polyurethanes according to the invention have an essentially linear backbone, i.e. they have no branching sites or few branching sites relative to the overall length. Branches thereof may be present in hydrophobic and/or hydrophilic sections. The polyurethanes PU according to the invention, however, are not star-shaped or crosslinked polyurethanes. Polyurethanes of this type and their preparation are known from the prior art and do not form part of this invention.

Preferably, the polyurethanes according to the invention have less than or equal to 4 branches per molecule, particularly preferably less than or equal to 3 branches per molecule. In a particularly preferred embodiment, the polyurethanes according to the invention have no branches outside of the edge-position sections T. Methods for determining branching, such as, for example, via NMR spectroscopy, are known to the person skilled in the art.

The backbone of the polyurethanes according to the invention is composed of alternating hydrophobic and hydrophilic sections, where the hydrophobic and hydrophilic sections alternate in the sequence, but may be different in terms of their size, length and nature. A hydrophilic section is attached on both sides directly to a hydrophobic section. These hydrophobic sections may, independently of one another, be different or else identical. Each section may be short-chain or an oligomer radical or a polymer radical.

Hydrophilic is the term used here to refer to those sections which exhibit marked interaction with water. In general, hydrophilic sections consist of radicals of substances which are themselves hydrophilic.

Typical hydrophilic groups known to the person skilled in the art are nonionic polyether radicals. Preferred polyether radicals comprise essentially unbranched alkylene oxide radicals.

Polyether radicals may be homo-alkylene oxide radicals, or comprise mixtures of different alkylene oxide radicals. These different alkylene oxide radicals may be present in random distribution in the polyether radicals or be present in block form.

Preferred polyether radicals are homo-ethylene oxide radicals or homo-propylene oxide radicals. According to another embodiment, the polyether radicals comprise mixtures of ethylene oxide radicals and propylene oxide radicals. These may be present in the polyether radicals in random distribution or be present in block form. A particularly preferred embodiment includes polyether radicals which have at least 50% by weight of ethylene oxide radicals, for example polyether radicals, which have more than 50% by weight of ethylene oxide radicals and, as further alkylene oxide radicals, propylene oxide radicals. The polyether radicals very particularly preferably consist of ethylene oxide radicals.

The hydrophilicity of a substance can be determined, for example, by means of an opacity measurement of an aqueous solution.

The hydrophobic sections present in the polyurethanes according to the invention behave oppositely toward water compared with the hydrophilic sections. In general, the hydrophobic sections consist of radicals of substances which are immiscible or only very poorly miscible with water and are virtually always lipophilic, i.e. they readily dissolve in nonpolar solvents, fats and oils.

Typical hydrophobic groups are, for example, hydrocarbon radicals, in particular long-chain hydrocarbon radicals. According to the invention, unbranched or slightly branched hydrocarbon radicals are preferred. According to one of the embodiments, the hydrocarbon radicals are unbranched. Long-chain aliphatic alcohols, aromatic alcohols and also aliphatic diisocyanates are examples of hydrophobic substances whose radicals may be present in the hydrophobic sections of the polyurethanes according to the invention.

A molecule which has both hydrophobic and hydrophilic sections is generally referred to as an amphiphilic molecule. Examples are, inter alia, phospholipids, emulsifiers and surfactants. One measure of the hydrophilicity of an amphiphilic compound is the HLB value. The HLB value (hydrophilic-lipophilic-balance) describes the hydrophilic and lipophilic proportion of mainly nonionic surfactants and was proposed in the 20th century by W. C. Griffin (Griffin, W. C.: Classification of surface active agents by HLB, J. Soc. Cosmet. Chem. 1, 1949).

The HLB value can be calculated as follows (see formula I):

$$HLB = 20 * \left(1 - \frac{M_1}{M}\right) \quad \text{(formula 1)}$$

where MI is the molar mass of the hydrophobic fraction of a molecule and M is the molar mass of the overall molecule. The factor 20 is a scaling factor freely chosen by Griffin. It thus usually results in a scale from 1 to 20. An HLB value of 1 denotes a lipophilic compound, a chemical compound with an HLB value of 20 has a high hydrophilic fraction.

The polyurethanes according to the invention preferably have an HLB value in accordance with Griffin of greater than or equal to 10, particularly preferably of greater than or equal to 14, on a scale from 1 to 20.

Polyurethanes according to the invention comprise at least two terminal hydrophobic sections (T). The polyurethanes PU according to the invention can be branched to a low degree in the interior of the molecule (if desired by using tri- or polyisocyanates in low fractions), so that then more than two terminal hydrophobic sections T could be present. Preferably, the polyurethanes PU according to the invention in the interior of the molecule are unbranched and comprise two terminal hydrophobic sections T. Their terminal position means that they are directly attached only to one further section of the polyurethanes according to the invention.

The terminal sections T may be identical or, independently of one another, different. The terminal hydrophobic sections T may be branched or unbranched. Preferably, at least one of the two terminal hydrophobic sections T of the polyurethanes PU according to the invention is branched.

Preferably, the terminal hydrophobic sections T comprise a chain of carbon atoms. Preferably, the chain length of the sections T is in the range from 4 to 30 carbon atoms, particularly preferably in the range from 6 to 26 and very particularly preferably in the range from 8 to 20 carbon atoms.

Such sections T can consist, for example, of aromatic radicals, but also of alkyl radicals. Thus, the sections T may be branched or unbranched alkyl radicals, or comprise these. Preferably, at least one section T is a branched alkyl radical. Branched means that branches attach to one or more carbon atoms of the alkyl radical. Usually, a branching of an alkyl means that, besides the members of the main chain, one or more additional carbon atoms are covalently bonded to one or two positions on a carbon atom of the carbon backbone, and form a side chain. The side chains may have identical or different sizes. Preferably, the side chains are themselves alkyl radicals or alkylene radicals, particularly preferably alkyl radicals, in particular unbranched alkyl radicals.

In one embodiment, the side chains of the alkyl radicals preferably have a chain length of not more than 6 carbon atoms. In another embodiment, the branches are preferably significantly shorter chains than the main chain. Preferably, each branch of the sections T of the polyurethanes according to the invention has at most a chain length which corresponds to half of the chain length of the main chain of this section T. The branched alkyl radicals are particularly preferably iso- and/or neo-alkyl radicals. Preferably, the chain length of the main chain of alkyl radicals which are present in sections T is in the range from 4 to 30 carbon atoms, for example alkyl radicals of butane, pentane, hexane, heptane, octane, nonane, decane, undecane, dodecane, tridecane, tetradecane, pentadecane, hexadecane, heptadecane, octadecane, nonadecane, icosane, henicosane, docosane, tricosane, tetracosane, pentacosane, hexacosane, heptacosane, octacosane, nonacosane and/or triacontane. Branched alkyl radicals of these alkanes may be used. Radicals of cycloalkanes or alkenes may likewise also be present. The sections T particularly preferably comprise alkyl radicals with a number of carbon atoms in the range from 6 to 26, for example radicals of hexane, heptane, octane, nonane, decane, undecane, dodecane, tridecane, tetradecane, pentadecane, hexadecane, heptadecane, octadecane, nonadecane, icosane, henicosane, docosane, tricosane, tetracosane, pentacosane and/or hexacosane, and very particularly preferably in the range from 8 to 20 carbon atoms, for example radicals of octane, nonane, decane, undecane, dodecane, tridecane, tetradecane, pentadecane, hexadecane, heptadecane, octadecane, nonadecane and/or icosane. Branched alkyl radicals of these alkanes can be used just as much as radicals of cycloalkanes or alkenes.

In a preferred embodiment, the branched alkyl radicals used are radicals of isoalkanes. Particular preference is given to a C13-alkyl radical, in particular an iso-C13 alkyl radical.

The sections T can be introduced into the polyurethanes according to the invention in various ways, for example as part of ethoxylated fatty alcohols.

Mixtures of polyurethanes PU whose terminal, hydrophobic sections T are branched and/or unbranched alkyl radicals are also in accordance with the invention. For example, also mixtures in which polyurethanes PU according to the invention are present which have both branched and unbranched terminal, hydrophobic sections T.

A hydrophilic section (S) is directly attached to each section T in polyurethanes according to the invention. The section S has a distancing effect as a so-called spacer S. A certain spatial flexibility of the sections S is desired. Preferably, the hydrophilic sections are unbranched.

In the polyurethanes PU according to the invention, the spacers S may be identical or, independently of one another, different. In one embodiment, the hydrophilic sections S are of various length and linear.

In a further preferred embodiment, the sections S have a chain length of from 5 to 100 atoms, preferably from 6 to 90 atoms and particularly from 8 to 80 atoms, in particular chains from 15 to 60 atoms.

The sections S can comprise radicals of alkylene oxides. Preferably, the number is in the range from 2 to 30 alkylene oxide radicals, particularly preferably in the range from 3 to 25 alkylene oxide radicals and very particularly preferably in the range from 3 to 20 alkylene oxide radicals.

According to the invention, the at least two hydrophilic sections S preferably consist of ethylene oxide radicals. In a preferred embodiment, the hydrophilic sections S comprise ethylene oxide radicals, the number of which is in the range from 2 to 30 radicals, particularly preferably in the range from 3 to 25 ethylene oxide radicals and very particularly preferably in the range from 3 to 20 radicals.

A mixture of ethylene oxide and propylene oxide radicals or only propylene oxide radicals in sections S are also possible.

Sections S can likewise comprise longer-chain alkylene oxide radicals, although it must be observed that the sections S must be hydrophilic overall (e.g. through a correspondingly high ethylene oxide fraction).

At least one hydrophobic section (D) is attached directly to at least one side on each hydrophilic section S. Here, a section S may also be present in the interior of the molecule of the polyurethanes according to the invention. In this case, this section S is connected not like an edge-position section S to a section D and a section T, but on at least two sides to sections D. Preferably, a section S is connected in the interior of the molecule on both sides to one section D in each case. For all edge-position sections S, it is the case that they are directly connected to an end-position section T.

Should a section S be branched to a low extent, then it could be directly connected at two or more positions to hydrophobic sections D. Preferably, in each case a hydrophobic section D is attached to each linear hydrophilic spacer S on one or two sides.

In a particularly preferred embodiment, all of the sections S, i.e. in particular the two sections S, are unbranched, edge-positioned, and connected to a section T on one side and to a section D on the other side.

According to the invention, the polyurethanes comprise at least two hydrophobic sections D. The hydrophobic sections D can be identical or, independently of one another, different.

The sections D can be branched with short-chain hydrophobic branches or be unbranched. Preferably, the sections D are unbranched.

Preferably, the sections D comprise a hydrophobic chain of carbon atoms, the length of which is in the range from 2 to 20 carbon atoms, preferably 3 to 16 carbon atoms and in particular in the range from 4 to 12 carbon atoms.

Preferably, the sections D comprise diisocyanate radicals. The sections D particularly preferably comprise radicals of aliphatic diisocyanates. Thus, for example, a hydrophobic section D can consist of one or more aliphatic diisocyanate radicals. Preferably, a section D consists of one to ten aliphatic diisocyanate radicals, particularly preferably of one to five aliphatic diisocyanate radicals, very particularly preferably it comprises one, two or three aliphatic diisocyanate radicals. The hydrophobic sections D can comprise aliphatic diisocyanate radicals with long, mid-length or short aliphatic units.

In one of the preferred embodiments, the sections D of the polyurethanes according to the invention are cycloaliphatic or aliphatic diisocyanate radicals. The sections D are particularly preferably aliphatic diisocyanate radicals.

Examples of aliphatic diisocyanates are: 1,4-butylene diisocyanate, 1,12-dodecamethylene diisocyanate, 1,10-decamethylene diisocyanate, 2-butyl-2-ethylpentamethylene diisocyanate, 2,4,4- or 2,2,4-trimethylhexamethylene diisocyanate and in particular hexamethylene diisocyanate (HDI).

Examples of cycloaliphatic diisocyanates are: isophorone diisocyanate (IPDI), 2-isocyanatopropylcyclohexyl isocyanate, 4-methylcyclohexane-1,3 diisocyanate (H-TDI) and 1,3-bis(isocyanatomethyl)cyclohexane. So-called $H_{12}$-MDI or diisocyanates termed "saturated MDI", such as, for example, 4,4'-methylenebis(cyclohexyl isocyanate) (alternatively also called dicyclohexylmethane 4,4'-diisocyanate) or 2,4'-methylenebis(cyclohexyl) diisocyanate can also be present as radicals in sections D of the polyurethanes PU according to the invention.

It is of course possible to use mixtures of the abovementioned diisocyanates in order to prepare mixtures of different polyurethanes PU according to the invention.

The polyurethanes according to the invention comprise at least one hydrophilic section (P). Here, at least one hydrophobic section D attaches directly to P on at least one side. The sections P of the polyurethanes according to the invention can be identical or, independently of one another, different.

If, in a polyurethane according to the invention, more than one section P is present, then at least one hydrophobic section D is located between the hydrophilic sections P. In one embodiment, polyurethanes according to the invention can comprise a sequence of sections in the order hydrophobic section D, then hydrophilic section S, then hydrophobic section D again between two hydrophilic sections P. Thus, if, in a polyurethane according to the invention, more than one section P is present, then in such case, the sections in the interior of the molecule can have a sequence of P-D-P or of P-D-S-D-P. Should more than two sections P be present, then both sequences in one molecule are possible. Preferably, only one or two sections P are present in a molecule of the polyurethanes according to the invention.

Preferably, the hydrophilic sections P are essentially linear polyether radicals, e.g. polyalkylene oxides. The hydrophilic sections P are particularly preferably radicals of polyetherdiols, in particular of polyethylene glycols. The at least one hydrophilic section P of the polyurethanes according to the invention is preferably composed of polyethylene oxide.

According to the invention, the essentially linear polyether radicals which form the sections P have to have a number-average molecular weight of at least 1500 g/mol. In general, the sections P have molecular weights of average size, e.g. up to 20 000 g/mol.

In a particularly preferred embodiment, the essentially linear polyether radicals have number-average molecular weights in the range from 1500 g/mol to 12 000 g/mol. Particularly preferably, the molecular weight of the sections P is less than or equal to 10 000 g/mol and particularly preferably in the range from 4000 g/mol to 9000 g/mol. The linear polyether radicals very particularly preferably have molecular weights of greater than or equal to 6000 g/mol.

All of the hydrophilic sections of the polyurethanes according to the invention, i.e. both sections S and also sections P, may be polyether radicals.

In a preferred embodiment, the hydrophilic sections of the polyurethanes according to the invention consist of
polyalkylene oxide units (sections P) and
polyethylene oxide units (sections S).

In a particularly preferred embodiment of the PU according to the invention, all of the sections P and S consist of polyethylene oxide units.

The backbone of the polyurethanes according to the invention comprises essentially radicals of polyethers and diisocyanates.

The polyurethanes according to the invention comprise at least three hydrophilic sections. In one of the preferred embodiments, these are two sections S and at least one section P.

In a particularly preferred embodiment, the sequence of the sections of the polyurethanes according to the invention is either T-S-D-P-D-S-T or T-S-D-P-D-P-D-S-T.

For each section P, its size is larger relative to the size of any spacer S present in the same molecule.

The ratio of the molecular weights of each hydrophilic section S of the polyurethanes according to the invention to the molecular weight of each hydrophilic section P is in the range from 1:1.4 to 1:140, preferably in the range from 1:1.7 to 1:120. In a preferred embodiment, the ratio is 1:x, where x is equal to or greater than 2, preferably equal to or greater than 2.3 and particularly preferably x is equal to or greater than 2.8. The ratio is particularly preferably in the range from 1:2.8 to 1:115, very particularly preferably in the range from 1:3 to 1:95 and particularly preferably in the range from 1:3.4 to 1:80.

Likewise in accordance with the invention are polyurethanes PU as described above, for which it is additionally the case that they are a mixture. Such a mixture can comprise, for example, polyurethanes which do have the same sequence of the sections T, S, D and/or P, but differ from one another structurally in at least one of the sections. One example of this which may be mentioned is a different section composition or a different section chain length. Thus, in a mixture of polyurethanes PU according to the invention, sections T may be different. For example, a mixture according to the invention can comprise polyurethanes whose sections T are both branched, and/or those whose sections T are both linear, and/or those polyurethanes which comprise a linear section T and a branched section T. Such mixtures can of course also comprise other substances, such as, for example, further, preferably water-dispersible polyurethanes not in accordance with the invention.

Such a mixture of polyurethanes PU can take place through the use corresponding to different feed materials or mixtures thereof in the preparation of the polyurethanes PU according to the invention, or be generated by subsequent mixing of only uniformly prepared polyurethanes according to the invention.

In one embodiment, the sum of the molecular weights of all sections T, plus the molecular weights of sections D is to be kept less than or equal to the sum of the molecular weights of all of the sections P.

Moreover, the invention provides a process for the preparation of polyurethanes PU according to the invention.

The polyurethanes PU according to the invention can be prepared in the absence or preferably in the presence of at least one catalyst.

Suitable catalysts are, for example, all catalysts customarily used in polyurethane chemistry.

Particular preference is given to using those catalysts which are soluble in organic solvents such as xylene, toluene, acetone, tetrahydrofuran (THF), butyl acetate, N-methylpyrrolidone and/or N-ethylpyrrolidone.

Catalysts usually used in polyurethane chemistry are organic amines, in particular tertiary aliphatic, cycloaliphatic or aromatic amines, and Lewis-acidic organic metal compounds.

Suitable Lewis-acidic organic metal compounds are, for example, metal complexes, such as acetyl acetonates of iron, titanium, zinc, aluminum, cobalt, manganese, nickel and zirconium, such as, for example, zirconium 2,2,6,6-tetramethyl-3,5-heptanedionate. Further suitable metal compounds are described by Blank et al. in Progress in Organic Coatings, 1999, 35, 19 ff.

Bismuth, cobalt or zinc catalysts, and also cesium or titanium salts can also be used as catalysts.

Preferably, the preparation of polyurethanes PU according to the invention takes place in the presence of compounds containing zinc and/or titanium. Particular preference is given to the presence of at least one zinc carboxylate or at least one titanium (IV) alcoholate or mixtures thereof in the preparation of the polyurethanes PU according to the invention.

In one embodiment of the invention, titanium alcoholates, preferably with a chain length of 2 or more carbon atoms, are used. In a preferred embodiment, the titanium alcoholates have a carbon chain of 20 or fewer carbon atoms. Preferably, the chain length of the titanium alcoholates is in the range from 3 to 18 carbon atoms. Particular preference is given to titanium alcoholates based on aliphatic alcohols. In a particularly preferred embodiment, the preparation of the polyurethanes PU according to the invention takes place in the presence of tetrabutyl orthotitanate, also known as titanium (IV) butylate or tetrabutoxytitanium.

In one preferred embodiment of the invention, the catalysts used are zinc carboxylates which are soluble in acetone, toluene, xylene and/or aliphatic hydrocarbons.

In a further preferred embodiment, the preparation of the polyurethanes PU according to the invention takes place in the presence of at least one zinc carboxylate in which the anion conforms to the formulae $(C_nH_{2n-1}O_2)^-$ or $(C_{n+1}H_{2n-2}O_4)^{2-}$ where n is 1 to 20. Particularly preferred zinc salts have, as anions, monocarboxylates of the general formula $(C_nH_{2n-1}O_2)^-$, where n is the numbers 1 to 20.

Preferably, the polyurethanes PU according to the invention are prepared in the presence of zinc carboxylates, which are aliphatic or aromatic carboxylates, and if desired can comprise one or two ring structures.

In a particularly preferred embodiment, the catalysts for the preparation of polyurethanes PU according to the invention are preferably zinc carboxylates whose carboxylic acid radicals have a carbon chain of 20 or fewer, preferably 18, particularly preferably less than or equal to 12 or fewer carbon atoms, since it has been found that in the case of long-chain carboxylate radicals, the activity of the catalyst in the process according to the invention decreases.

In one embodiment, zinc carboxylates without ring structure can be used as catalysts for preparing polyurethanes according to the invention. Particular preference is given to using aliphatic zinc carboxylates as catalysts.

As catalysts for use in processes according to the invention for preparing polyurethanes PU according to the invention, very particular preference is given to using zinc 2-ethylhexanoate (also called zinc octanoate), zinc n-octanoate, zinc n-decanoate, zinc neodecanoate, zinc ricinoleate and zinc stearate. Particular preference is given to using zinc neodecanoate.

It is of course also possible to use mixtures of two or more of the abovementioned compounds as catalysts for the preparation of polyurethanes PU according to the invention.

Preference is given to using a catalyst.

The amount of the catalyst used does not play a role per se. In general, a cost-effective amount of catalyst is used. Consequently, the catalyst or the mixture of the catalysts is preferably used in an amount in the range from 100 ppm to 10 000 ppm, based on the total weight of the polyetherdiols used. For the preparation of the polyurethanes PU according to the invention, catalyst is preferably used in an amount in the range from 500 to 5000 ppm, particularly preferably in an amount of less than or equal to 4500 ppm, based on the total weight of the polyetherdiols used. In one particularly preferred embodiment, an amount of catalyst in the range from 1000 ppm to 3000 ppm, based on the total weight of the polyetherdiols used is used for the preparation of the polyurethanes according to the invention.

The catalyst or catalysts can be added to the processes according to the invention in solid or liquid form or in dissolved form, depending on the nature of the catalyst or the catalysts. Suitable solvents are water-immiscible solvents, such as aromatic or aliphatic hydrocarbons, inter alia toluene, xylene, ethyl acetate, hexane and cyclohexane, and also carboxylic acid esters, such as, for example, ethyl acetate. Furthermore, suitable solvents are acetone, THF and N-methylpyrrolidone and N-ethylpyrrolidone. Preferably, the catalyst or catalysts are added in solid or liquid form. Preferably, the catalyst is used in dissolved form in a solvent, very particularly preferably dissolved in organic solvents such as aliphatic hydrocarbons, acetone, toluene or xylene.

In a particularly preferred embodiment of the invention, the catalyst or catalysts is/are used in dissolved form.

In a further particularly preferred embodiment of the invention, the catalyst used is zinc carboxylates which are dissolved in aliphatic hydrocarbons, acetone, toluene, xylene or optionally mixtures thereof.

The polyurethanes PU according to the invention are prepared by a process according to the invention in which the synthesis takes place in two stages. If desired, the second reaction stage is followed by a work-up of the products.

In principle, the reaction can also be carried out without catalyst, although the products are generally more difficult to reproduce (with regard, for example, to the number-average and weight-average molecular weights), the reaction times are generally significantly longer and the viscosities achieved in preparations which comprise water are sometimes lower. In some cases, the increased formation of (high molecular weight) by-products resulted in crosslinking when no catalyst was present. Preferably, in the processes according to the invention, at least one, particularly preferably precisely one, catalyst is used.

One advantage of the processes according to the invention for the preparation of polyurethanes PU in this preferred embodiment is the fact that the product comprises uniformly structured molecules or a clearly defined mixture of polyurethane molecules.

In one embodiment, the process according to the invention for the preparation of polyurethanes PU can comprise the following steps:
1. at least one polyetherdiol with a molecular weight of at least 1500 g/mol is reacted with at least one aliphatic diisocyanate and in the presence of at least one zinc carboxylate and/or at least one titanium alcoholate;
2. then the intermediates produced are reacted with at least one ethoxylated fatty alcohol;
3. then the work-up takes place, i.e. generally the removal of all organic solvents and the transfer of the polymer to water.

In the processes according to the invention, the reaction of the starting materials can take place in solution. A reaction in the melt is also possible, in which case the feed materials are present not in dissolved form or for the greatest part not in dissolved form in solvents.

In one preferred embodiment of the process according to the invention, the reaction is carried out in two steps in solution, particularly preferably dissolved in organic solvents such as acetone, toluene or xylene.

Preferably, polyetherdiol which is as anhydrous as possible is used in the first step of the processes according to the invention. The removal of the water from the polyether can take place in processes according to the invention by azeotropic distillation, drying in vacuo or other methods known to the person skilled in the art. For example, through azeotropic distillation it is possible to remove water until the water content prior to the addition of the diisocyanates is approximately 300 ppm. The preparation of the actual reaction can, for example, consist of
either placing the polyetherdiol under reduced pressure and thus removing the water sufficiently (preferably to a water content of approximately 300 ppm or less), and then admixing a solvent, or
mixing the polyetherdiol with a solvent such as xylene, toluene or acetone and removing the water by azeotropic distillation, for example to a water content of approximately 300 ppm, where, however, the solvent is not removed completely, but the solution of polyether in the remaining solvent is used for the reaction in solution.

Prior to the reaction with diisocyanates, the pH of the diol solution in solvent can be adjusted to a value of less than or equal to pH 7 and, if desired, be buffered, for example by desalting or addition of one acid or a mixture of different acids. Suitable acids are inorganic or organic acids, e.g. hydrochloric acid, sulfuric acid, sulfurous acid, nitric acid, phosphoric acid, hydrofluoric acid, carbonic acid, organic acids, such as malic acid, citric acid, oxalic acid, formic acid, acetic acid, propionic acid, butyric acid, The ethoxylated fatty alcohols used in the process according to the invention preferably have a degree of ethoxylation which is at least in the range from 2 to 30 radicals, particularly preferably in the range from 3 to 25 ethylene oxide radicals and very particularly preferably in the range from 3 to 20 radicals. At least one of the fatty alcohols used is in most cases preferably a branched, nonionic compound prepared from a saturated iso-C13 alcohol of the structural formula $RO(CH_2CH_2O)_xH$, where R is a C13 alkyl radical, preferably an iso-C13-alkyl radical, and where x=3, 5, 6, 6.5, 7, 8, 10, 12, 15 or 20, preferably x=10 (commercially available from BASF SE under the name "Lutensol® TO" e.g. when x=10 as "Lutensol® TO10").

In the process according to the invention, the ratio (mol to mol) of the polyetherdiols used to diisocyanates used can be in the range from 1:1.1 to 1:1.9. Preferably, the ratio is in the range from 1:1.1 to 1:1.8. The ratio is particularly preferably in the range from 1:1.1 to 1:1.75. The ratio is especially preferably in the range from 1:1.2 to 1:1.75. The ratio can of course also be 1:x where x is greater than or equal to 1.3, preferably x is greater than or equal to 1.5.

In one embodiment, this results in only one or two sections P preferably being present in one molecule of the polyurethanes according to the invention.

In a specific embodiment of the process according to the invention (mol to mol), in addition to the said ranges of the ratio of polyetherdiols to diisocyanates, the ratio of polyetherdiols to ethoxylated fatty alcohols is additionally chosen so that the ratio of polyetherdiols used to ethoxylated fatty alcohols used is in the range from 5:1 to 1:2. Preferably, this ratio is in the range from 2:1 to 1:1.8, particularly preferably in the range from 1:1 to 1:1.6 and most preferably 1:1.5.

For all three feed materials of the process according to the invention, it is the case that a ratio (mol to mol) of polyetherdiols to diisocyanates to ethoxylated fatty alcohols of 1:1.75:1.5 is very particularly preferably used.

The invention also provides the use of the polyurethanes PU according to the invention and polyurethanes prepared according to the invention for producing preparations which comprise water. Preference is given here to preparations which comprise at least 5% by weight, in particular at least 20% by weight, very particularly preferably at least 30% by weight and most preferably at least 50% by weight, of water. The preparations comprising water may be, for example, solutions, emulsions, suspensions or dispersions.

In addition to the polyurethanes PU according to the invention and polyurethanes prepared according to the invention, other substances can also be used according to the invention for producing preparations, such as, for example, customary auxiliaries (for example dispersants and/or stabilizers), surfactants, preservatives, antifoams, fragrances, wetting agents, thickeners, dyes, softeners, humectants and/or other polymers.

Preferably, the polyurethanes PU according to the invention and mixtures of polyurethanes produced according to the invention can be used in order to produce preparations comprising water which comprise at least one salt or at least one surfactant or mixtures thereof.

Within the context of the present invention, surfactants are also understood as meaning emulsifiers and mixtures of surfactants and emulsifiers. Within the context of the present invention, salt is understood as meaning salts and also salt-like structures also with a low $pK_a$ value and mixtures thereof.

The polyurethanes PU according to the invention and polyurethanes prepared according to the invention are particularly preferably used in order to produce preparations which comprise at least 0.05% by weight of salt and/or at least 0.5% by weight of surfactants, very particularly preferably at least 0.1% (w/w) of salt and/or at least 1% by weight of surfactants.

In a further embodiment, the polyurethanes PU according to the invention and polyurethanes prepared according to the invention are used in order to produce preparations which comprise up to 20% by weight of salt, preferably up to 10% by weight and particularly preferably 5% by weight or less of salt. In a further embodiment, the polyurethanes PU according to the invention and polyurethanes produced according to the invention are used to produce preparations which comprise up to 25% by weight of surfactants, preferably up to 20% by weight and particularly preferably 15% by weight or fewer surfactants.

In a further embodiment, the polyurethanes PU according to the invention and polyurethanes prepared according to the invention are used to produce preparations which comprise up to 10% by weight of salt, preferably up to 5% by weight of salt and up to 20% by weight of surfactants, preferably up to 15% by weight of surfactants.

The polyurethanes PU according to the invention and polyurethanes prepared according to the invention are particularly preferably used to produce preparations which are oil-in-water emulsions. Typically, oil-in-water emulsions comprise an oil fraction greater than 0% by weight and less than or equal to 40% by weight. According to the invention, oil-in-water emulsions are preferably prepared which comprise an oil fraction in the range from 5 to 40% by weight, particularly in the range from 10 to 35% by weight and in particular from 15 to 30% by weight, of oil.

The polyurethanes PU according to the invention and polyurethanes prepared according to the invention are very particularly preferably used for producing preparations which are oil-in-water emulsions and comprise at least one salt.

The preparations according to the invention which comprise a polyurethane according to the invention may be solutions, emulsions, suspensions or dispersions, for example. In one embodiment, a preparation according to the invention is a dispersion, preferably an aqueous dispersion, of the polyurethanes PU according to the invention, as can be obtained from the reaction products by the preparation process by work-up. For this, for example, the solvent is removed and water is added and a dispersion is produced. If desired, a preservative and/or stabilizer may also be added.

In one of the embodiments, the dispersion according to the invention comprises up to 25% by weight of the polyurethanes according to the invention. In another embodiment, the dispersion comprises 20% by weight of solids fraction.

In addition, the dispersion according to the invention can comprise at least one preservative and/or at least one stabilizer which protects against free radicals. Very particular preference is given to aqueous dispersions comprising up to 20% (w/v) of the polyurethanes according to the invention, a preservative suitable for cosmetic applications and, if desired, at least one stabilizer suitable for cosmetic applications which protects against free radicals. Suitable preservatives and free-radical stabilizers, such as, for example, tocopherol (but not limited to these) are known to the person skilled in the art.

To produce the preparations according to the invention, which may, for example, be solutions, emulsions, suspensions or dispersions, the polyurethanes according to the invention are preferably used in the form of aqueous dispersions, as can be obtained from the preparation process through work-up (for example by removing the solvent, adding water and, if desired, by adding a preservative and/or a stabilizer).

In a further embodiment, further substances as are customarily used in preparations may be present in preparations according to the invention depending on the field of use of the preparation. Such substances are, without listing them exhaustively, customary auxiliaries (for example dispersants and/or stabilizers), surfactants, preservatives, antifoams, fragrances, wetting agents, thickeners, dyes and/or other polymers. Such further additives e.g. in the field of cosmetic preparations, emulsion paints or preparations of crop protectants are known to the person skilled in the art. According to the invention, it is preferred to use no further thickeners besides the polyurethanes according to the invention for producing preparations comprising water.

The polyurethanes PU according to the invention have various advantages. One advantage is their property of changing the rheological properties of a preparation according to the invention which comprises PU.

In quite general terms, modification of the rheological properties is understood as meaning the change in the shaping and flow behavior of material. One of the most important rheological properties is the viscosity. This term is known to the person skilled in the art.

Viscosity is usually understood as meaning the "ropiness" of a liquid. It results from the intermolecular forces in a liquid, is thus dependent on cohesion (intramolecular) and adhesion (intermolecular). The viscosity characterizes the flow behavior of a liquid. High viscosity means thick liquid, whereas low means thin liquid.

Modifying the rheology is understood in particular as meaning the increase in the viscosity of liquids, usually also referred to as "thickening". This viscosity increase can extend to the formation of gels or solids.

Preference is given to polyurethanes PU according to the invention which lead to an increase in the dynamic viscosity of preparations comprising water. They can be regarded as an alternative solution to the set object—modification of the rheological properties of preparations comprising water—to thickeners from the prior art.

Preference is given to polyurethanes PU whose 10 percent strength by weight aqueous dispersions have a dynamic viscosity, measured as described below at a shear rate of 100 1/s, of at least 100 mPa*s, particularly preferably of at least 200 mPa*s and very particularly preferably of at least 300 mPa*s. The aqueous dispersions of the polyurethanes PU according to the invention here can exhibit either Newtonian behavior or else non-Newtonian behavior. Non-Newtonian dispersions which comprise the polyurethanes PU according to the invention preferably have dynamic viscosities of at least 1000 mPa*s, particularly preferably even of at least 3000 mPa*s (10% strength by weight aqueous dispersions, measured as described below at a shear rate of 100 1/s).

The person skilled in the art is aware that in preparations comprising water, many thickeners forfeit their effect, i.e. the viscosity of the preparation drops as soon as the preparations likewise comprise salt and/or surfactant. By contrast, in a preferred embodiment, the polyurethanes PU according to the invention lead to a stabilization of the viscosity of preparations comprising water even with added salt and/or surfactant. Particular preference is given to polyurethanes PU according to the invention which, at a salt concentration of greater than or equal to 0.5% by weight, following addition lead to a stabilization of the dynamic viscosity, measured as described below, of preparations comprising water. Particular preference is given to those polyurethanes which lead to a stabilization of the dynamic viscosity upon the addition of greater than or equal to 0.5% by weight of salt and the addition of greater than or equal to 1% by weight of surfactant, the order of the additions, if desired, being unimportant.

In a further embodiment, the viscosity of preparations comprising water which comprise at least one salt is increased through the presence of the polyurethanes PU according to the invention in the preparation compared to preparations which comprise only salt or only polyurethanes PU according to the invention. Here, the order in which polyurethanes PU according to the invention and salt are added is unimportant. Particular preference is given to polyurethanes PU according to the invention which lead to an increase in the dynamic viscosity, measured as described below, of preparations comprising water if at least one salt or at least one surfactant or mixtures thereof are present in the preparations. In particular, preference is given to polyurethanes PU according to the invention which, at a salt concentration of greater than or equal to 0.5% by weight, lead to an increase in the dynamic viscosity, measured as described below, of preparations comprising water. Particular preference is given to those polyurethanes which lead to an increase in the dynamic viscosity compared to preparations which comprise less than 0.5% by weight, preferably 0.1% by weight, of salt, or less than 1% by weight, preferably 0.5% by weight, of surfactant.

Very particular preference is given to polyurethanes PU according to the invention which, at a salt concentration of greater than or equal to 0.05% by weight, lead to an increase in the dynamic viscosity, measured as described below, of preparations comprising water. Particular preference is given to those polyurethanes which lead to an increase in the dynamic viscosity compared to preparations which comprise less than 0.05% by weight, preferably less than or equal to 0.01% by weight, of salt, or less than 0.5% by weight, preferably less than or equal to 0.1% by weight, of surfactant.

A further advantage of the polyurethanes according to the invention is the micelle formation in water. The critical micelle concentration (CMC) indicates the concentration of a substance, mostly of a substance which has hydrophobic and hydrophilic sections on the inside, at which micelles are spontaneously formed. The CMC of the polyurethanes according to the invention in water, determined as described below, is preferably less than or equal to 1 g/l, particularly preferably less than or equal to 0.5 g/l, especially preferably less than or equal to 0.25 g/l and very particularly preferably less than or equal to 0.1 g/l.

A further advantage of the polyurethanes according to the invention, of the processes according to the invention for their preparation and of the preparations according to the invention is the preferred use of zinc-containing and/or titanium-containing catalysts in the preparation of the polyurethanes PU. Particularly in the field of cosmetic preparations, the processes known from the prior art using tin are no longer desired since tin may also be present in the products and the preparations resulting therefrom. Zinc-containing additives of cosmetic preparations are accepted, where zinc can, if appropriate, confer additional advantages through its antibacterial and anti-inflammatory properties.

On account of their tolerance toward high salt contents and simultaneously high surfactant contents even at extreme pH values, the polyurethanes PU according to the invention can advantageously also be used as thickeners in home-care preparations, such as, for example, liquid cleaners.

In particular, the polyurethanes PU according to the invention are also exceptionally suitable as rheology modifiers for preparations containing hydrogen peroxide.

The invention will be illustrated in more detail by reference to the following nonlimiting examples.

EXAMPLES

Unless stated otherwise, all of the percentages are percentages by weight.
Determination of the Dynamic Viscosity The dynamic viscosities of the polyurethanes PU according to the invention in aqueous dispersion were measured in the form of a 10 percent strength by weight dispersion at 23° C. In the examples listed below, the dynamic viscosity was for this purpose always determined at shear rates of 100 1/s and 350 1/s. These two values allow a statement to be made as to whether the polyurethanes PU according to the invention exhibit non-Newtonian or Newtonian thickening behavior in aqueous dispersion. The following were used for determining the dynamic viscosity in accordance with DIN53019:

Instrument used: Physica Rheolab MCI portable rotary viscometer from Anton Paar;
Cylinder measurement system, Z4 DIN cylinder (diameter 14 mm)
Instrument used: Physica Rheolab MCI portable rotary viscometer from Anton Paar;
cylinder measurement system, Z4 DIN cylinder (diameter 14 mm)

Synthesis Example 1

Preparation of Polyurethanes PU.1

17.75 kg of a linear polyethylene glycol with a number-average molecular weight of 6000 g/mol (e.g. Pluriol® E6000 from BASF SE) were dissolved in 23.50 kg of xylene under nitrogen. After heating the solution to about 140° C., xylene was distilled off so that the water content of the reaction mixture was then only about 140 ppm.

The polymer solution was now cooled to 50° C. and admixed with 13.1 g of acetic acid, dissolved in 500 ml of xylene, in order to buffer the amount of potassium acetate in the polyethylene glycol which had been quantitatively determined beforehand. By adding 37.28 g of zinc neodecanoate, dissolved in a mixture of aliphatic hydrocarbons and xylene, and 870.0 g of hexamethylene diisocyanate, dissolved in xylene, the polymerization was started and the mixture was left to react at 50° C. until the isocyanate content was 0.27% by weight.

A mixture of 1.42 kg of a nonionic ethoxylated fatty alcohol, prepared from a saturated iso-C13 alcohol and an average degree of ethoxylation of 10 (e.g. Lutensol® TO10 from BASF SE), and 1.64 kg of a nonionic ethoxylated fatty alcohol mixture, prepared from a saturated C16/C18 alcohol mixture and an average degree of ethoxylation of 11 (e.g. Lutensol® AT11 from BASF SE), dissolved in xylene, was then added. The reaction mixture was further heated at 50° C. until the isocyanate content was 0% by weight. The solvent xylene was subsequently removed by vacuum distillation at elevated temperature down to a residual content of below 500 ppm. The resulting product PU.1 is a mixture which comprises linear polyurethanes with edge-position branched and/or unbranched sections T. The ratio of the molecular weights of a hydrophilic section S to the molecular weight of a hydrophilic section P in the polyurethanes PU.1 is typically 1:12.4 or 1:13.6. The latter ratio arises for sections S which consist of 10 ethylene oxide radicals, and the first for those which are composed of 11 ethylene oxide radicals.

The molar ratio of sections P to D is 1:1.75.

The product PU.1 was dispersed in 86.73 kg of water and cooled to room temperature (25° C.). The mixture of polymers PU.1 (Mn=17 600 g/mol; Mw=30 500 g/mol) was in the form of an aqueous dispersion which had a solids content of 20.5% by weight. The viscosity of a 10% strength by weight aqueous dispersion of the polyether polyurethanes PU.1 at 23° C. was 7700 mPa*s (shear rate 100 1/s) or 5900 mPa*s (shear rate 350 1/s) and exhibited slightly non-Newtonian behavior.

Synthesis Example 2

Preparation of Polyurethanes PU.2

17.75 kg of a linear polyethylene glycol with a number-average molecular weight of 6000 g/mol (e.g. Pluriol® E6000 from BASF SE) were dissolved in 23.50 kg of xylene under nitrogen. After heating the solution to about 140° C., xylene was distilled off so that the water content of the reaction mixture was then only still about 250 ppm.

The polymer solution was then cooled to 50° C. and admixed with 13.1 g of acetic acid, dissolved in 500 ml of xylene, in order to buffer the amount of potassium acetate in the polyethylene glycol which had been quantitatively determined beforehand.

By adding 37.28 g of zinc neodecanoate, dissolved in a mixture of aliphatic hydrocarbons and xylene, and 870.0 g of hexamethylene diisocyanate, dissolved in xylene, the polymerization was started and the mixture was left to react at 50° C. until the isocyanate content was 0.29% by weight.

A mixture of 0.95 kg of a nonionic ethoxylated fatty alcohol, prepared from a saturated iso-C13 alcohol and an average degree of ethoxylation of 10 (e.g. Lutensol® TO10 from BASF SE), and 2.19 kg of a nonionic ethoxylated fatty alcohol, prepared from a saturated C16/C18 alcohol mixture and an average degree of ethoxylation of 11 (e.g. Lutensol® AT11 from BASF SE), dissolved in xylene, was then added and the reaction mixture was further heated at 50° C. until the isocyanate content was 0% by weight. The solvent xylene was subsequently removed by vacuum distillation at elevated temperature down to a residual content of below 500 ppm.

The resulting product PU.2 is a mixture which comprises linear polyurethanes with edge-position branched and/or unbranched sections T. The ratio of the molecular weights of a hydrophilic section S to the molecular weight of a hydrophilic section P in the polyurethanes PU.2 is typically 1:12.4 or 1:13.6. The latter ratio arises for sections S which consist of 10 ethylene oxide radicals, the former for those which are composed of 11 ethylene oxide radicals.

The molar ratio of sections P to D is 1:1.75.

The product PU.2 was dispersed in 87.02 kg of water and cooled to room temperature (25° C.). The polymer mixture PU.2 (Mn=16 700 g/mol; Mw=29 500 g/mol) was in the form of an aqueous dispersion which had a solids content of 20.0% by weight. The viscosity of a 10% strength by weight aqueous dispersion of the polyether polyurethanes PU.2 at 23° C. was 26 200 mPa*s (shear rate 100 1/s) or 12 800 mPa*s (shear rate 350 1/s) and exhibited marked non-Newtonian behavior.

Synthesis Example 3

Preparation of Polyurethanes PU.3

120.00 g of a linear polyethylene glycol with a number-average molecular weight of 6000 g/mol (e.g. Pluriol® E6000 from BASF SE) were dissolved in 467.00 g of xylene under nitrogen. After heating the solution to about 140° C., xylene was distilled off so that the water content of the reaction mixture was then less than 300 ppm.

The polymer solution was then cooled to 50° C. By adding 42 mg of zinc neodecanoate, dissolved in a mixture of aliphatic hydrocarbons, and 5.88 g of hexamethylene diisocyanate, dissolved in xylene, the polymerization was started and the mixture was left to react at 50° C. until the isocyanate content was 0.25% by weight.

19.20 g of a nonionic ethoxylated fatty alcohol, prepared from a saturated iso-C13 alcohol and an average degree of ethoxylation of 10 (e.g. Lutensol® TO10 from BASF SE), dissolved in xylene, were then added and the reaction mixture was further heated at 50° C. until the isocyanate content was 0% by weight. The solvent xylene was then removed by vacuum distillation at elevated temperature down to a residual content of below 500 ppm.

The resulting product PU.3 is a mixture which comprises linear polyurethanes with edge-position branched sections T. The ratio of the'molecular weights of a hydrophilic section S to the molecular weight of a hydrophilic section P in the polyurethanes PU.3 is typically 1:13.6. This ratio arises for sections S which consist of 10 ethylene oxide radicals.

The molar ratio of sections P to D is 1:1.75.

The product PU.3 was dispersed in 580.3 g of water and cooled to room temperature (25° C.). The polymer mixture PU.3 (Mn=27 200 g/mol; Mw=51 900 g/mol) was in the form of an aqueous dispersion which had a solids content of 20.0%. The viscosity of a 10% strength by weight aqueous dispersion of the polyether polyurethanes PU.3 at 23° C. was 680 mPa*s (shear rate 100 1/s) or 640 mPa*s (shear rate 350 1/s) and exhibited Newtonian thickening behavior.

Synthesis Example 4

Preparation of Polyurethanes PU.4

17.75 kg of a linear polyethylene glycol with a number-average molecular weight of 6000 g/mol (e.g. Pluriol® E6000 from BASF SE) were dissolved in 23.50 kg of xylene under nitrogen. After heating the solution to about 140° C., xylene was distilled off so that the water content of the reaction mixture was then about 120 ppm.

The polymer solution was then cooled to 50° C. and admixed with 13.1 g of acetic acid, dissolved in 500 ml of xylene, in order to buffer the amount of potassium acetate in the polyethylene glycol which had been quantitatively determined beforehand.

By adding 37.28 g of zinc neodecanoate, dissolved in a mixture of aliphatic hydrocarbons and xylene, and 870.0 g of hexamethylene diisocyanate, dissolved in xylene, the polymerization was started and the mixture was left to react at 50° C. until the isocyanate content was 0.26% by weight.

2.84 kg of a nonionic ethoxylated fatty alcohol, prepared from a saturated iso-C13 alcohol and an average degree of ethoxylation of 10 (e.g. Lutensol® TO10 from BASF SE), dissolved in xylene, were then added and the reaction mixture was further heated at 50° C. until the isocyanate content was 0% by weight. The solvent xylene was then removed by vacuum distillation at elevated temperature until the residual content was below 500 ppm.

The resulting product PU.4 is a mixture which comprises linear polyurethanes with edge-position branched sections T. The ratio of the molecular weights of a hydrophilic section S to the molecular weight of a hydrophilic section P in the polyurethanes PU.4 is typically 1:13.6. This ratio arises for sections S which consist of 10 ethylene oxide radicals.

The molar ratio of sections P to D is 1:1.75.

The product PU.4 was dispersed in 85.84 kg of water and cooled to room temperature (25° C.). The polymer mixture PU.4 (Mn=19 200 g/mol; Mw=30 800 g/mol) was in the form of an aqueous dispersion which had a solids content of 18.1%. The viscosity of a 10% strength by weight aqueous dispersion of the polyether polyurethanes PU.4 at 23° C. was 600 mPa*s (shear rate 100 1/s) or 570 mPa*s (shear rate 350 1/s) and exhibited Newtonian thickening behavior.

Synthesis Example 5

Preparation of Polyurethanes PU.5

240.00 g of a linear polyethylene glycol with a molecular weight of 6000 g/mol (e.g. Pluriol® E6000 from BASF SE) were dissolved in 934.00 g of xylene under nitrogen. After heating the solution to about 140° C., xylene was distilled off so that the water content of the reaction mixture was then less than 300 ppm.

The polymer solution was then cooled to 50° C. By adding 84 mg of zinc neodecanoate, dissolved in aliphatic hydrocarbons, and 11.76 g of hexamethylene diisocyanate, dissolved in xylene, the polymerization was started and the mixture was left to react at 50° C. until the isocyanate content was 0.22% by weight.

20.70 g of a nonionic ethoxylated fatty alcohol, prepared from a saturated C13 alcohol and an average degree of ethoxylation of 3 (e.g. Lutensol® AO3 from BASF SE), dissolved in xylene, were then added and the reaction mixture was further heated at 50° C. until the isocyanate content was 0% by weight. The solvent xylene was then removed by vacuum distillation at elevated temperature until the residual content was below 500 ppm and the residue was then dispersed in 1089.8 g of water.

The ratio of the molecular weights of a hydrophilic section S to the molecular weight of a' hydrophilic section P in the polyurethanes PU.5 is typically 1:45.5. This ratio arises for the sections S which consist of 3 ethylene oxide radicals.

The molar ratio of sections P to D is 1:1.75.

After cooling to room temperature (25° C.), the polymers PU.5 (Mn=21 300 g/mol; Mw=36 300 g/mol) were in the form of an aqueous dispersion which had a solids content of 20.1% by weight. The viscosity of a 10% strength by weight aqueous dispersion of the polyether polyurethanes PU.5 at 23° C. was 10 900 mPa*s (shear rate 100 1/s) or 9200 mPa*s (shear rate 350 1/s) and exhibited weakly non-Newtonian behavior.

Synthesis Example 6

Preparation of Polyurethanes PU.6

180.00 g of a linear polyethylene glycol with a molecular weight of 6000 g/mol (e.g. Pluriol® E6000 from BASF SE) were dissolved in 180.00 g of acetone under nitrogen. After heating the solution to reflux (internal temperature about 56° C.), a further 1362.4 g of acetone were continuously added and, at the same time, a total of 1362.4 g of acetone were distilled off. The water content of the reaction mixture was then only still about 240 ppm.

The polymer solution was then cooled to 50° C. By adding 189 mg of zinc neodecanoate, dissolved in aliphatic hydrocarbons, and 8.82 g of hexamethylene diisocyanate, dissolved in acetone, the polymerization was started and the mixture was left to react at 50° C. until the isocyanate content was 0.33% by weight.

15.53 g of a nonionic ethoxylated fatty alcohol, prepared from a saturated C13 alcohol and an average degree of ethoxylation of 3 (e.g. Lutensol® AO3 from BASF SE), dissolved in acetone, were then added and the reaction mixture was further heated at 50° C. until the isocyanate content was 0% by weight. The solvent acetone was then removed by vacuum distillation down to a residual content of below 500 ppm and the residue was dispersed in 817.4 g of water.

The ratio of the molecular weights of a hydrophilic section S to the molecular weight of a hydrophilic section P in the polyurethanes PU.6 is typically 1:45.5. This ratio arises for the sections S which consist of 3 ethylene oxide radicals.

The molar ratio of sections P to D is 1:1.75.

After cooling to room temperature (25° C.), the polymers PU.6 (Mn=24 900 g/mol; Mw=40 000 g/mol) were in the form of an aqueous dispersion which had a solids content of 19.6% by weight. The viscosity of a 10% strength by weight aqueous dispersion of the polyether polyurethanes PU.6 at 23° C. was 8800 mPa*s (shear rate 100 1/s) or 7800 mPa*s (shear rate 350 1/s) and exhibited slightly non-Newtonian behavior.

Synthesis Example 7

Preparation of Polyurethanes PU.7

120.00 g of a linear polyethylene glycol with a number-average molecular weight of 6000 g/mol (e.g. Pluriol® E6000 from BASF SE) were dissolved in 467.00 g of xylene under nitrogen. After heating the solution to about 140° C., xylene was distilled off so that the water content of the reaction mixture was then only still about 120 ppm.

The polymer solution was then cooled to 50° C. and admixed with 107 mg of acetic acid, dissolved in 5 ml of xylene, in order to buffer the amount of potassium acetate in the polyethylene glycol which had been quantitatively determined beforehand. By adding 252 mg of zinc neodecanoate, dissolved in a mixture of aliphatic hydrocarbons and xylene, and 5.88 g of hexamethylene diisocyanate, dissolved in xylene, the polymerization was started and the mixture was left to react at 50° C. until the isocyanate content was 0.25% by weight.

22.20 g of a nonionic ethoxylated fatty alcohol mixture, prepared from a saturated C16/C18 alcohol mixture and an average degree of ethoxylation of 11 (e.g. Lutensol® AT11 from BASF SE), dissolved in xylene, were then added. The reaction mixture was further heated at 50° C. until the isocyanate content was 0% by weight. The solvent xylene was then removed by vacuum distillation at elevated temperature down to a residual content of below 500 ppm.

The resulting product PU.7 is a mixture which comprises linear polyurethanes with edge-position, unbranched sections T. The ratio of the molecular weights of a hydrophilic section S to the molecular weight of a hydrophilic section P in the polyurethanes PU.7 is typically 1:12.4. This ratio arises for sections S which consist of 11 ethylene oxide radicals.

The molar ratio of sections P to D is 1:1.75.

The product PU.7 was dispersed in 592.3 g of water and cooled to room temperature (25° C.). The mixture of polymers PU.7 (Mn=18 700 g/mol; Mw=30 900 g/mol) was in the form of an aqueous dispersion which had a solids content of 20.4% by weight. The viscosity of a 10% strength by weight aqueous dispersion of the polyether polyurethanes PU.7 at 23° C. was 35 500 mPa*s (shear rate 100 1/s) or 14 500 mPa*s (shear rate 350 1/s) and exhibited strongly non-Newtonian behavior.

Synthesis Example 8

Preparation of Polyurethanes PU.8

180.00 g of a linear polyethylene glycol with a number-average molecular weight of 9000 g/mol (e.g. Pluriol® E9000 from BASF SE) were dissolved in 467.00 g of xylene under nitrogen. After heating the solution to about 140° C., xylene was distilled off so that the water content of the reaction mixture was then only still about 70 ppm.

The polymer solution was then cooled to 50° C. and admixed with 208 mg of acetic acid, dissolved in 5 ml of xylene, in order to buffer the amount of potassium acetate in the polyethylene glycol which had been quantitatively determined beforehand. By adding 378 mg of zinc neodecanoate, dissolved in a mixture of aliphatic hydrocarbons and xylene, and 5.88 g of hexamethylene diisocyanate, dissolved in xylene, the polymerization was started and the mixture was allowed to react at 50° C. until the isocyanate content was 0.27% by weight.

10.20 g of a nonionic ethoxylated fatty alcohol, prepared from a saturated iso-C13 alcohol and an average degree of ethoxylation of 3 (e.g. Lutensol® TO3 from BASF SE), dissolved in xylene, were then added. The reaction mixture was further heated at 50° C. until the isocyanate content was 0% by weight. The solvent xylene was then removed by vacuum distillation at elevated temperature until the residual content was below 500 ppm.

The resulting product PU.8 is a mixture which comprises linear polyurethanes with edge-position branched sections T. The ratio of the molecular weights of a hydrophilic section S to the molecular weight of a hydrophilic section P in the polyurethanes PU.8 is typically 1:68.2. This ratio arises for sections S which consist of 3 ethylene oxide radicals.

The molar ratio of sections P to D is 1:1.75.

The product PU.8 was dispersed in 784.3 g of water and cooled to room temperature (25° C.). The mixture of polymers PU.8 (Mn=27 300 g/mol; Mw=46 500 g/mol) was in the form of an aqueous dispersion which had a solids content of 20.2% by weight. The viscosity of a 10% strength by weight aqueous dispersion of the polyether polyurethanes PU.8 at 23° C. was 1060 mPa*s (shear rate 100 1/s & shear rate 350 1/s) and exhibited marked Newtonian behavior.

Synthesis Example 9

Preparation of Polyurethanes PU.9

180.00 g of a linear polyethylene glycol with a number-average molecular weight of 9000 g/mol (e.g. Pluriol® E9000 from BASF SE) were dissolved in 467.00 g of xylene under nitrogen. After heating the solution to about 140° C., xylene was distilled off so that the water content of the reaction mixture was then only still about 70 ppm.

The polymer solution was then cooled to 50° C. and admixed with 208 mg of acetic acid, dissolved in 5 ml of xylene, in order to buffer the amount of potassium acetate in the polyethylene glycol that had been quantitatively determined beforehand. By adding 378 mg of zinc neodecanoate, dissolved in a mixture of aliphatic hydrocarbons and xylene, and 5.88 g of hexamethylene diisocyanate, dissolved in xylene, the polymerization was started and the mixture was left to react at 50° C. until the isocyanate content was 0.28% by weight.

A mixture of 5.10 g of a nonionic ethoxylated fatty alcohol, prepared from a saturated iso-C13 alcohol and an average degree of ethoxylation of 3 (e.g. Lutensol® TO3 from BASF SE), and 11.10 g of a nonionic ethoxylated fatty alcohol mixture, prepared from a saturated C16/C18 alcohol mixture and an average degree of ethoxylation of 11 (e.g. Lutensol® AT11 from BASF SE), dissolved in xylene, was then added. The reaction mixture was further heated at 50° C. until the isocyanate content was 0% by weight. The solvent xylene was then removed by vacuum distillation at elevated temperature down to a residual content of below 500 ppm.

The resulting product PU.9 is a mixture which comprises linear polyurethanes with edge-position branched and/or unbranched sections T. The ratio of the molecular weights of a hydrophilic section S to the molecular weight of a hydrophilic section P in the polyurethanes PU.9 is typically 1:12.4 or 1:68.2. The last-mentioned ratio results for sections S which consist of 3 ethylene oxide radicals, the former for those which are composed of 11 ethylene oxide radicals.

The molar ratio of sections P to D is 1:1.75.

The product PU.9 was dispersed in 764.0 g of water and cooled to room temperature (25° C.). The mixture of polymers PU.9 (Mn=25 000 g/mol; Mw=45 500 g/mol) was in the form of an aqueous dispersion which had a solids content of 20.8% by weight. The viscosity of a 10% strength by weight aqueous dispersion of the polyether polyurethanes PU.9 at 23° C. was 7500 mPa*s (shear rate 100 1/s) or 4500 mPa*s (shear rate 350 1/s) and exhibited strongly non-Newtonian behavior.

Synthesis Example 10

Preparation of Polyurethanes PU.10

120.00 g of a linear polyethylene glycol with a number-average molecular weight of 1500 g/mol (e.g. Pluriol® E1500 from BASF SE) were dissolved in 467.00 g of xylene under nitrogen. After heating the solution to about 140° C., xylene was distilled off so that the water content of the reaction mixture was then only still about 110 ppm.

The polymer solution was then cooled to 50° C. and admixed with 90 mg of acetic acid, dissolved in 5 ml of xylene, in order to buffer the amount of potassium acetate within the polyethylene glycol which had been quantitatively determined beforehand. By adding 252 mg of zinc neodecanoate, dissolved in a mixture of aliphatic hydrocarbons and xylene, and 15.72 g of hexamethylene diisocyanate, dissolved in xylene, the polymerization was started and the mixture was left to react at 50° C. until the isocyanate content was 0.29% by weight.

17.41 g of a nonionic ethoxylated fatty alcohol, prepared from a saturated iso-C13 alcohol and an average degree of ethoxylation of 10 (e.g. Lutensol® TO10 from BASF SE), dissolved in xylene, were then added. The reaction mixture was further heated at 50° C. until the isocyanate content was 0% by weight. The solvent xylene was subsequently removed by vacuum distillation at elevated temperature down to a residual content of below 500 ppm.

The resulting product PU.10 is a mixture which comprises linear polyurethanes with edge-position branched sections T. The ratio of the molecular weights of a hydrophilic section S to the molecular weight of a hydrophilic section P in the polyurethanes PU.10 is typically 1:13.6. This ratio arises for sections S which consist of 10 ethylene oxide radicals.

The molar ratio of sections P to D is 1:1.17.

The product PU.10 was dispersed in 612.5 g of water and cooled to room temperature (25° C.). The mixture of polymers PU.10 (Mn=18 600 g/mol; Mw=34 900 g/mol) was in the form of an aqueous dispersion which had a solids content of 20.1% by weight. The viscosity of a 10% strength by weight aqueous dispersion of the polyether polyurethanes PU.10 at 23° C. was 165 mPa*s (shear rate 100 1/s & shear rate 350 1/s) and exhibited marked Newtonian behavior.

Synthesis Example 11

Preparation of Polyurethanes PU.11

90.00 g of a linear polyethylene glycol with a number-average molecular weight of 1500 g/mol (e.g. Pluriol® E1500 from BASF SE) were dissolved in 467.00 g of xylene under nitrogen. After heating the solution to about 140° C., xylene was distilled off so that the water content of the reaction mixture was then only still about 80 ppm.

The polymer solution was then cooled to 50° C. and admixed with 68 mg of acetic acid, dissolved in 5 ml of xylene, in order to buffer the amount of potassium acetate within the polyethylene glycol which had been quantitatively determined beforehand. By adding 189 mg of zinc neodecanoate, dissolved in a mixture of aliphatic hydrocarbons and xylene, and 17.64 g of hexamethylene diisocyanate, dissolved in xylene, the polymerization was started and the mixture was left to react at 50° C. until the isocyanate content was 0.97% by weight.

99.00 g of a nonionic ethoxylated fatty alcohol, prepared from a saturated iso-C13 alcohol and an average degree of ethoxylation of 20 (e.g. Lutensol® TO20 from BASF SE), dissolved in xylene, were then added. The reaction mixture was further heated at 50° C. until the isocyanate content was 0% by weight. The solvent xylene was then removed by vacuum distillation at elevated temperature down to a residual content of below 500 ppm.

The resulting product PU.11 is a mixture which comprises linear polyurethanes with edge-position branched sections T. The ratio of the molecular weights of a hydrophilic section S to the molecular weight of a hydrophilic section P in the polyurethanes PU.11 is typically 1:1.7. This ratio arises for sections S which consist of 20 ethylene oxide radicals.

The molar ratio of sections P to D is 1:1.75.

The product PU.11 was dispersed in 826.6 g of water and cooled to room temperature (25° C.). The mixture of polymers PU.11 (Mn=4000 g/mol; Mw=9000 g/mol) was in the form of an aqueous dispersion which had a solids content of 20.0% by weight. The viscosity of a 10% strength by weight aqueous dispersion of the polyether polyurethanes PU.11 at 23° C. was 150 mPa*s (shear rate 100 1/s & shear rate 350 1/s) and exhibited marked non-Newtonian behavior.

Determination of the Critical Micelle Concentration

The CMC of the polyurethanes according to the invention in water was determined using the dynamic light scattering method.

For this, a goniometer SP-86 (ALV-Laser Vertriebsgesellschaft mbH, Langen, Germany) was used as combined DLS/SLS unit. The unit also comprised an ALV 5000 correlator and a He—Ne laser of wavelength 633 nm (both likewise ALV, Langen). The conditions used for the measurement series comprising concentrations of from 0.0001 g/l to 10 g/l were a measurement angle of 90° at a temperature of 23° C. The evaluation was carried out with the help of the program known in the prior art called CONTIN (Constrained Inversion) with intensity distribution (CONTIN likewise from ALV, Langen).

Comparative Example

A nonionic, hydrophobically modified, ethoxylated urethane of the prior art prepared from stearyl alcohol, a diisocyanate and a polyethylene glycol (sold by Rohm & Haas as Aculyn® 46) was used in the comparison for determining the CMC. Aculyn® 46 had no measurable CMC. At concentrations of from 0.001 to 10 g/l, relatively large undefined aggregates in the range 100 to 500 nm were always present as main component.

CMC of the Polyurethanes of the Present Invention:

For the mixtures of polyurethanes PU.1 and also PU.2 prepared in synthesis example 1 and 2, it was found that, at 0.1 g/l, defined micelles with average particle diameters of 30 nm were present. The CMC for both was therefore less than 0.1 g/l. For the polyurethanes PU.4 according to the invention prepared in synthesis example 4, it was found that, at a concentration of PU.4 of 1 g/l, micelles with diameter of 17 nm were present, and at a concentration of 0.1 g/l, both micelles of an average size of 15 nm and also a smaller fraction of undefined aggregates of a size of approximately 200 nm existed alongside one another. Consequently, in this case too, a CMC of <0.1 g/l was present.

Preparation Example 1

Preparation of Cosmetic Preparations Using the Polyurethanes PU.1 to PU.5 with a Nonionic Base (P.1.1 to P.1.5)

The cosmetic preparations were prepared by adding the water phase B to the oil phase A and subsequently admixing the resulting O/W emulsion with the preservative (phase C).This gave the nonionic-based preparations P.1.1 to P.1.5. (Tab. 1).

TABLE 1

Composition of the nonionic-based cosmetic preparations P.1.1 to P.1.5.

| Phase | Ingredients | P.1.1 | P.1.2 | P.1.3 | P.1.4 | P.1.5 |
|---|---|---|---|---|---|---|
| Phase A | Ceteareth-6, stearyl alcohol | 2.0 g | 2.0 g | 2.0 g | 2.0 g | 2.0 g |
| | Ceteareth-25 | 2.0 g | 2.0 g | 2.0 g | 2.0 g | 2.0 g |
| | Cetearyl alcohol | 2.5 g | 2.5 g | 2.5 g | 2.5 g | 2.5 g |
| | Paraffin oil | 5.0 g | 5.0 g | 5.0 g | 5.0 g | 5.0 g |
| | Cetearyl ethylhexanoate | 5.0 g | 5.0 g | 5.0 g | 5.0 g | 5.0 g |

TABLE 1-continued

Composition of the nonionic-based cosmetic preparations P.1.1 to P.1.5.

| Phase | Ingredients | P.1.1 | P.1.2 | P.1.3 | P.1.4 | P.1.5 |
|---|---|---|---|---|---|---|
| Phase B | PU | PU.1 | PU.2 | PU.3 | PU.4 | PU.5 |
| | | 0.5 g | 0.5 g | 2.0 g | 2.0 g | 0.5 g |
| | 1,2-propylene glycol | 5.0 g | 5.0 g | 5.0 g | 5.0 g | 5.0 g |
| | Water | 77.5 g | 77.5 g | 76.0 g | 76.0 g | 77.5 g |
| Phase C | Preservative: Euxyl ® K300 (phenoxyethanol, methylparaben, ethylparaben, butylparaben, propylparaben, isobutylparaben), commercially available from Fischer-Chemie, Wiesbaden | 0.5 g | 0.5 g | 0.5 g | 0.5 g | 0.5 g |

Preparation Example 2

Preparation of Cosmetic Preparations Using the Polyurethanes PU.1 to PU.5; Nonionic-Base (P.2.1 to P.2.5)

The cosmetic preparations were prepared by adding the water phase B to the oil phase A and subsequently admixing the resulting O/W emulsion with the preservative (phase C). This gave the nonionic-based preparations P.2.1-P.2.5. (Tab. 2).

TABLE 2

Composition of the nonionic-based cosmetic preparations P.2.1-P.2.5.

| Phase | Ingredients | P.2.1 | P.2.2 | P.2.3 | P.2.4 | P.2.5 |
|---|---|---|---|---|---|---|
| Phase A | Glyceryl stearate | 2.0 g | 2.0 g | 2.0 g | 2.0 g | 2.0 g |
| | Stearyl alcohol | 2.0 g | 2.0 g | 2.0 g | 2.0 g | 2.0 g |
| | Cyclopentasiloxane, cyclohexasiloxane | 3.0 g | 3.0 g | 3.0 g | 3.0 g | 3.0 g |
| | Dicaprylyl ether | 3.0 g | 3.0 g | 3.0 g | 3.0 g | 3.0 g |
| | Dimethicone | 2.0 g | 2.0 g | 2.0 g | 2.0 g | 2.0 g |
| | Aluminum starch octenylsuccinate | 1.0 g | 1.0 g | 1.0 g | 1.0g | 1.0 g |
| | PEG-40 stearate | 2.0 g | 2.0 g | 2.0 g | 2.0 g | 2.0 g |
| Phase B | PU | PU.1 | PU.2 | PU.3 | PU.4 | PU.5 |
| | | 0.5 g | 0.5 g | 2.0 g | 2.0 g | 0.5 g |
| | Glycerol | 5.0 g | 5.0 g | 5.0 g | 5.0 g | 5.0 g |
| | Water | 79.0 g | 79.0 g | 77.5 g | 77.5 g | 79.0 g |
| Phase C | Preservative: Euxyl ® K300 (phenoxyethanol, methylparaben, ethylparaben, butylparaben, propylparaben, isobutylparaben), commercially available from Fischer-Chemie, Wiesbaden | 0.5 g | 0.5 g | 0.5 g | 0.5 g | 0.5 g |

Determination of the Dynamic Viscosity of Preparations with Auxiliaries

The dynamic viscosity of preparations comprising water which comprise further auxiliaries, e.g. those cosmetic preparations which are disclosed in a nonlimiting manner in the preparation examples, was determined with the help of a Brookfield viscometer (Brookfield), model DV-II+Pro viscometer (model: RVDVII+Pro). The measurement system used was a RV spindle set at a temperature of 20° C. and 20 rpm shear rate.

Viscosities of the cosmetic preparations P.1.1 to P.1.5 (nonionic-based) as a function of the salt concentration

TABLE 3

Viscosities of the cosmetic preparations P.1.1 to P.1.5 as a function of the salt concentration.

| | Dynamic viscosity [Pa * s] | | | | |
|---|---|---|---|---|---|
| Preparation | 0% by wt. NaCl | 0.5% by wt. NaCl | 2.0% by wt. NaCl | 5.0% by wt. NaCl | 10.0% by wt. NaCl |
| P.1.1 | 33.2 | 24.0 | 13.2 | 7.9 | 7.0 |
| P.1.2 | 39.5 | 29.8 | 14.8 | 11.0 | 11.3 |

TABLE 3-continued

Viscosities of the cosmetic preparations P.1.1 to P.1.5 as a function of the salt concentration.

| Preparation | Dynamic viscosity [Pa * s] | | | | |
|---|---|---|---|---|---|
| | 0% by wt. NaCl | 0.5% by wt. NaCl | 2.0% by wt. NaCl | 5.0% by wt. NaCl | 10.0% by wt. NaCl |
| P.1.3 | 4.1 | 6.1 | 6.3 | 7.7 | 8.6 |
| P.1.4 | 3.0 | 4.3 | 3.9 | 4.3 | 2.4 |
| P.1.5 | 11.3 | 9.7 | 6.9 | 5.1 | 3.8 |

In the case of added salt, the preparations P.1.3 and P.1.4 exhibit increasing and/or largely stable viscosities. P.1.1, P.1.2 and P.1.5 still exhibit a good thickening effect even in the case of a moderate addition of salt.

Viscosities of the cosmetic preparations P.2.1. to P.2.5 (nonionic-based) as a function of the salt concentration

TABLE 4

Viscosities of the cosmetic preparations P.2.1 to P.2.5 as a function of the salt concentration.

| Preparation | Dynamic viscosity [Pa * s] | | | | |
|---|---|---|---|---|---|
| | 0% by wt. NaCl | 0.5% by wt. NaCl | 2.0% by wt. NaCl | 5.0% by wt. NaCl | 10.0% by wt. NaCl |
| P.2.1 | 23.3 | 18.0 | 15.0 | 10.6 | 5.3 |
| P.2.2 | 16.4 | 11.2 | 9.5 | 7.6 | 4.6 |
| P.2.3 | 13.1 | 14.4 | 15.6 | 18.0 | 20.3 |
| P.2.4 | 5.4 | 13.0 | 13.3 | 15.2 | 13.7 |
| P.2.5 | 27.0 | 30.6 | 23.5 | 23.8 | 16.1 |

In the case of added salt, preparation P.2.5 exhibits stable and sometimes even increasing viscosities. This is even more marked for P.2.3 and P.2.4, these exhibit a large increase in the dynamic viscosities with the addition of salt up to 10% by weight. P.2.1 and P.2.2 still have a good thickening effect even in the case of a moderate addition of salt.

The invention claimed is:

1. A water-dispersible polyurethane (PU), prepared in the presence of at least one zinc carboxylate or at least one titanium alcoholate or mixtures thereof, with an essentially linear backbone composed of alternating hydrophilic and hydrophobic sections, where
   a. the polyurethane comprises two terminal sections (T) which are hydrophobic,
   b. each section T is directly attached to a hydrophilic section (S),
   c. each section S is directly attached to at least one hydrophobic section (D) on at least one side, and
   d. where at least one hydrophilic section (P) is present, where at least one hydrophobic section D attaches directly to P on at least one side of P, where at least one hydrophobic section D separates two sections P if more than one section P is present,
      and the polyurethane comprises at least three hydrophilic sections, and the ratio of the molecular weights of each hydrophilic section S to the molecular weight of each hydrophilic section P is from 1:1.4 to 1:140, the at least two hydrophobic sections D are hexamethylene diisocyanate radicals and the at least one hydrophilic section P is a polyether radical; wherein
the polyurethane comprises the reaction product of:
   a. a linear polyethylene glycol with a number-average molecular weight of 6000 g/mol;
   b. hexamethylene diisocyante;
   c. a non-ionic ethoxylated fatty alcohol, prepared from a saturated iso-C13 alcohol with an average degree of ethoxylation of 10; and
   d. a nonionic ethoxylated fatty alcohol, prepared from a saturated C16/C18 alcohol mixture with an average degree of ethoxylation of 11.

2. A preparation comprising at least one polyurethane according to claim 1.

3. The preparation according to claim 2, wherein the preparation is an aqueous dispersion.

* * * * *